United States Patent [19]

Andrew

[11] Patent Number: 5,197,877
[45] Date of Patent: Mar. 30, 1993

[54] IMPLEMENT FOR EXTRACTING DENTAL CROWNS, BRIDGES AND THE LIKE

[76] Inventor: Vladimir Andrew, 39, Allée Robertsau, F-6700 Strasbourg, France

[21] Appl. No.: 745,599

[22] Filed: Aug. 15, 1991

[30] Foreign Application Priority Data

Aug. 15, 1990 [CH] Switzerland ................... 02657/90
Jul. 26, 1991 [CH] Switzerland ................... 02252/91

[51] Int. Cl.$^5$ ............................................. A61C 3/00
[52] U.S. Cl. ................................. 433/153; 433/159; 433/157
[58] Field of Search ............... 433/153, 154, 157, 158, 433/159, 161

[56] References Cited

U.S. PATENT DOCUMENTS

| | | | |
|---|---|---|---|
| 3,377,704 | 4/1968 | Brodie et al. | 32/43 |
| 3,579,834 | 5/1971 | Reed, Jr. | 433/154 |
| 3,834,026 | 9/1974 | Klein | 32/43 |
| 4,197,647 | 4/1980 | Goldenthal | 433/159 |
| 4,417,876 | 11/1983 | Lynch | 433/161 |
| 4,474,500 | 10/1984 | Lynch | 433/161 |
| 5,015,185 | 5/1991 | Cané et al. | 433/153 |

FOREIGN PATENT DOCUMENTS

| | | |
|---|---|---|
| 3406514 | 9/1985 | Fed. Rep. of Germany. |
| 8810805 | 12/1988 | Fed. Rep. of Germany. |
| 3808880 | 9/1989 | Fed. Rep. of Germany. |
| 831750 | 3/1960 | United Kingdom ................ 433/159 |

*Primary Examiner*—Cary E. O'Connor
*Attorney, Agent, or Firm*—Peter K. Kontler

[57] ABSTRACT

An implement for extraction of crowns or bridges from the mouths of dental patients has one or more pairs of jaws and/or one or more hooks or a flexible wire engageable with a crown or bridge at a distance from the edge of the crown or bridge and at a distance from the gums of the patient, and a force applying unit which can pull the jaws and/or the hook or hooks or the wire in a direction to lift the crown or the bridge off the respective tooth or teeth. The jaws can engage spaced-apart portions of external surfaces of crowns, and the hook or hooks or the wire can engage the connector or connectors between neighboring crowns of a bridge.

19 Claims, 4 Drawing Sheets

FIG. 8
FIG. 9
FIG. 10
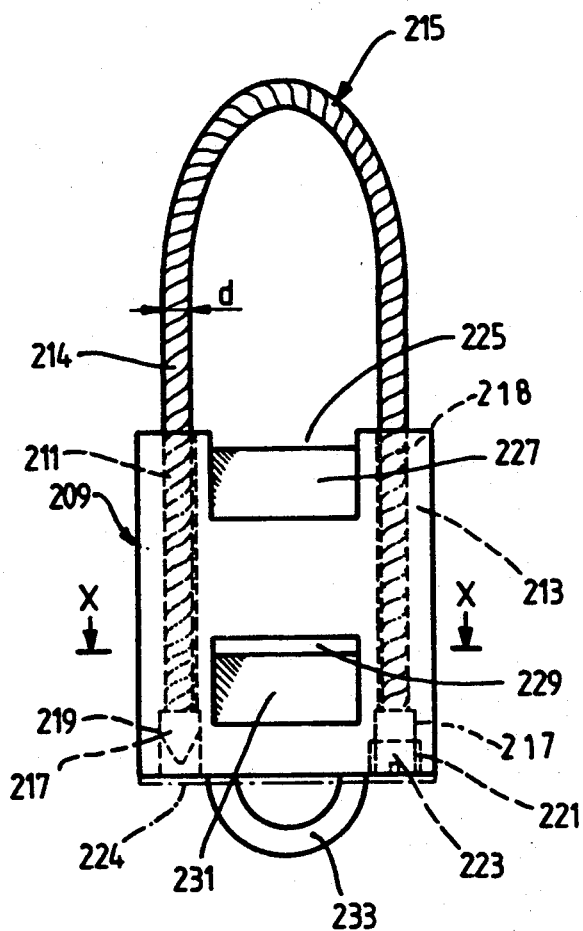
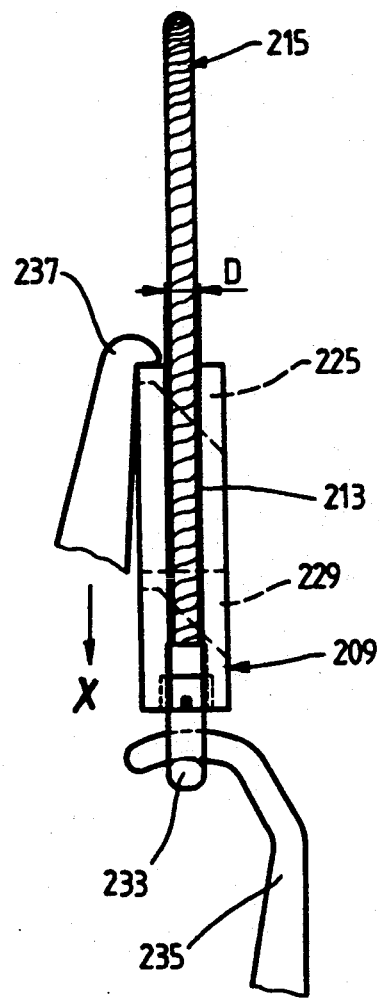
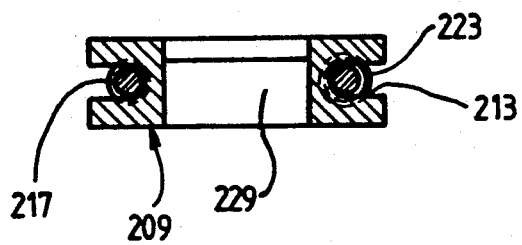

IMPLEMENT FOR EXTRACTING DENTAL CROWNS, BRIDGES AND THE LIKE

BACKGROUND OF THE INVENTION

The invention relates to implements or instruments for extracting bridges, crowns and/or other dental restorations or prostheses from the mouths of dental patients.

Extraction of bridges, crowns and similar prostheses is a task which must be carried out by a physician or by a skilled technician. The implements which are presently available for the performance of such tasks are not entirely satisfactory. As a rule, a presently known implement includes or constitutes a hook which is caused to engage the edge bounding an opening of the bridge or crown adjacent the gums of the wearer, and the implement is thereupon pulled, either steadily or in stages or steps, in a direction to lift the crown or the bridge off the material which bonds the prosthesis to the tooth or teeth of the patient. The crowns or bridges are normally made of a metallic material or a metal-ceramic compound. Removal of such prostheses is necessary in the event of damage, excessive wear, inflammation or infection of the gums or teeth and/or damage to the material which bonds the prosthesis to the tooth or teeth.

A drawback of an implement which employs or constitutes a hook is that it is highly likely to damage the gums of and to cause great discomfort to the wearer of a prosthesis. Moreover, and since the wall of a crown or bridge is normally extremely thin (as a rule, the thickness is in the range of 0.2 mm), the hook is likely to damage the edge which is engaged thereby and which is acted upon by the hook during separation of the prosthesis from the bonding material within and/or around it. Still further, the hook is highly likely to tilt the prosthesis and to thus cause even more damage as well as to encounter greater resistance as the extracting operation proceeds. Such tilting causes extensive damage to the tooth or teeth and to the bonding material between the tooth or teeth and the prosthesis. The situation is not changed if the extraction takes place in stages, e.g., by resorting to a hammer which repeatedly strikes an anvil at that end of the handle for the hook which is remote from the prosthesis. Injury to the gums as a result of engagement of a hook with the edge of a bridge or crown can cause inflammation or infection which must heal before the removed prosthesis or a fresh prosthesis can be inserted into the mouth.

Any, even slight, damage to a crown or bridge during extraction must be attended to subsequent to extraction at a considerable cost. The damage arises not only at the edge which is engaged by the hook but also at the ceramic coating (if any), and additional damage is observable on the bonding material.

German Utility Model No. G 88 108 805.8 of (published Dec. 1988) discloses a looped wire the ends of which are held in a housing and which is to be placed around a connection between two joined crowns of a bridge. The housing carries a guide for a reciprocable hammer which is caused to repeatedly strike an anvil in order to loosen the bridge preparatory to complete extraction from the mouth of a wearer. The implement of the German Utility Model exhibits the drawback that it is difficult to secure the looped wire to the housing subsequent to placing of the wire around the connection between two crowns of a bridge.

OBJECTS OF THE INVENTION

An object of the invention is to provide a simple, compact and inexpensive implement for extraction of prostheses (such as crowns or bridges) from the mouth of a patient.

Another object of the invention is to provide an implement which is less likely to damage a prosthesis than heretofore known implements.

A further object of the invention is to provide an implement which is designed to avoid injury to the gums and to avoid damage to the bonding material between the prosthesis and to the tooth or teeth of a patient.

An additional object of the invention is to provide an implement which is constructed and assembled and can be used in such a way that it is less likely to change the orientation of a prosthesis during extraction from the mouth of a patient.

Still another object of the invention is to provide an implement which is designed to simultaneously engage a prosthesis at a plurality of different locations.

A further object of the invention is to provide an implement which need not touch the gums of the wearer of a prosthesis or an edge of the prosthesis preparatory to and/or during extraction of the prosthesis.

Another object of the invention is to provide an implement which can engage and exert a pull upon a defective, worn and/or otherwise affected prosthesis in a number of different ways.

An additional object of the invention is to provide a novel and improved method of extracting bridges, crowns or other types of dental prostheses or dental restorations from the mouths of the wearers without the risk of injury, infection and/or damage to the prosthesis and/or bonding material.

A further object of the invention is to provide a method which facilitates rapid and painless extraction of prostheses.

Still another object of the invention is to provide an implement or instrument which is simple to use and easy to take apart for the purposes of cleaning, inspection or modification.

A further object of the invention is to provide an implement which can be manipulated to extract a crown or a bridge in such a way that the extracted part can be reinserted without the need for any repair work attributable to extraction from the mouth of the patient.

SUMMARY OF THE INVENTION

The invention resides in the provision of an implement or instrument for extracting dental prostheses (e.g., damaged crowns or bridges) of the type affixed to at least one tooth and having at least one portion which is spaced apart from the gums of the wearer of the prosthesis. The at least one portion can include two spaced-apart sections of the external surface at opposite sides of a crown or the bonded (e.g., soldered) connector or connection between two neighboring crowns of a bridge. The improved implement comprises a first unit including at least one extracting member or element which is engageable with the at least one portion of a prosthesis to be extracted, and a second unit including means for applying to the at least one extracting element a force in a direction away from the gums of the wearer to thereby separate the prosthesis from the at least one tooth.

The at least one extracting element can include a hook which can be caused to engage the aforementioned bonded connection between two crowns, and the force applying means of such implement can comprise a handle which is rigid with or is articulately connected to the hook.

Alternatively, the first unit can include two extracting elements and each such extracting element can include a jaw. The force applying means can include means for moving the jaws between first (spaced apart) positions in which the jaws provide room for the at least one portion of a prosthesis between them, and second (closed or operative) positions in which the jaws clamp the at least one portion of the prosthesis between them; the jaws can engage two portions of the aforementioned external surface at opposite sides of a crown). At least one of the jaws can comprise an elastic prosthesis-engaging portion or pad. Alternatively, at least one of the jaws can be provided with a roughened prosthesis-engaging surface; the surface can be roughened by being serrated and/or by being connected with (e.g., by having embedded therein) minute fragments of diamonds or another very hard substance.

The jaws can be provided with elongated arms, and the moving means can comprise a sleeve which surrounds and is slidable along the arms. The sleeve can be replaced with an internally threaded nut which surrounds the arms of the jaws.

It is also possible to employ an implement in the form of shears having two elongated halves each including a handle at one end and carrying one of the jaws at the other end. The shears further comprise means for pivotally connecting the two halves to each other intermediate the ends of the halves.

If the first unit includes a plurality of extracting elements (e.g., one or more pairs of jaws and/or one or more hooks), the force applying means can include means for movably coupling the extracting elements to each other. Such coupling means can include at least one annular member and/or at least one weighbeam.

The at least one extracting element can include an elongated flexible element having a first end and a second end, and the force applying means of such implement preferably comprises a housing having means for anchoring the ends of the flexible element therein subsequent to looping of the flexible element around the at least one portion of a prosthesis to be extracted, e.g., around the aforementioned bonded connection between two neighboring crowns. The ends of the flexible element can include or constitute heads, and the anchoring means can include two spaced-apart sockets which are provided in the housing, one for each end of the flexible element and each having an enlarged portion for the respective head. The anchoring means can further comprise means for releasably confining at least one of the heads in the enlarged portion of the respective socket. Such confining means can comprise a screw or another threaded member which mates with the housing and prevents extraction of the one head from the enlarged portion of the respective socket. Alternatively, the confining means can comprise a closure (e.g., a lever, a washer or the like) which overlies the enlarged portion of at least one of the sockets.

The flexible element can include a length of metallic wire having a first diameter which is slightly smaller than the diameters of holes or bores which are provided in the housing and each of which forms part of one of the sockets. The diameter of at least one of the heads can exceed the diameter of a hole or bore.

The second unit can further comprise means (such as a standard dentist's tool with a handle and a hook at one end or at each end of the handle) for pulling the housing. To this end, the housing preferably comprises at least one portion (e.g., a recess, a hole and/or a yoke) which is engageable by the pulling means.

The novel features which are considered as characteristic of the invention are set forth in particular in the appended claims. The improved implement itself, however, both as to its construction and the mode of utilizing the same, together with additional features and advantages thereof, will be best understood upon perusal of the following detailed description of certain presently preferred specific embodiments with reference to the accompanying drawing.

BRIEF DESCRIPTION OF THE DRAWING

FIG. 8 is a side elevational view of an implement which can be used for the extraction of bridges and wherein the first unit comprises an elongated flexible element;

FIG. 9 is an end elevational view of the implement of FIG. 8, and further showing two hook-shaped devices which can be used to exert a pull in a direction to extract a bridge from the mouth of the wearer; and FIG. 10 is a sectional view substantially as seen in the direction of arrows from the line X—X of FIG. 8.

DESCRIPTION OF PREFERRED EMBODIMENTS

Figure 1:
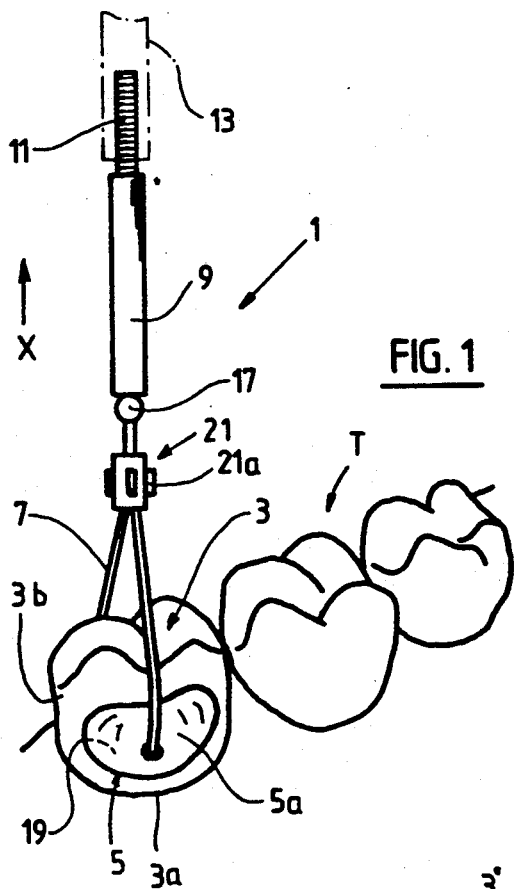
FIG. 1 is a perspective view of a portion of a first extracting implement wherein the first unit comprises two extracting elements in the form of jaws which are in the process of engaging two spaced apart portions of the external surface of a crown.

FIG. 1 shows a portion of an implement 1 which is designed to extract crowns 3 from the mouths of patients. The illustrated crown 3 is assumed to surround a portion of a tooth and is further assumed to be secured to such tooth portion by any suitable bonding material, not shown. The crown 3 has an opening surrounded by an edge 3a which is closely or immediately adjacent to the gums on the upper or lower jaw of the patient.

The implement 1 comprises a first unit composed of two extracting elements in the form of substantially kidney-shaped jaws 5 (one shown) each of which is provided with an arm 7. The arms 7 preferably exhibit or can exhibit a tendency to move the crown-engaging portions or pads 5a of the respective jaws 5 away from each other in order to provide room for positioning of the first unit of the implement 1 in a manner as shown in FIG. 1, i.e., so that the surfaces 19 of the pads 5a can engage two spaced apart portions of the external surface 3b of the crown 3 at locations which are spaced apart from the edge 3a, i.e., the jaws 5 need not come in contact with the gums.

Those ends of the arms 7 which are remote from the respective surfaces 19 are connected to an annular member or eyelet 17 forming part of a second unit of the implement 1. A sleeve 21 of the second unit surrounds the arms 7 and is movable along the arms toward and away from the annular member 17 in order to permit the pads 5a of the jaws 5 to move apart or to compel the pads 5a to move toward each other and to firmly engage the adjacent portions of the external surface 3b of the crown 3. The sleeve 21 can carry one or more screws 21a or other suitable fastener or detent means to releasably hold the sleeve in a selected position, particularly in a position in which the surfaces 19 of the pads 5a of the jaws 5 are in pronounced frictional engagement with the adjacent portions of the external surface 3b of the crown 3. The surfaces 19 can be provided on elastic portions or inserts of the pads 5a of the jaws 5, or such surfaces can be serrated and/or provided with embedded fragments of industrial diamonds or with embedded or adhesively secured fragments of other hard material which ensures the establishment of a reliable frictional engagement with the crown 3 when the sleeve 21 is caused to slide toward the crown between the two jaws 5.

Figure 3:
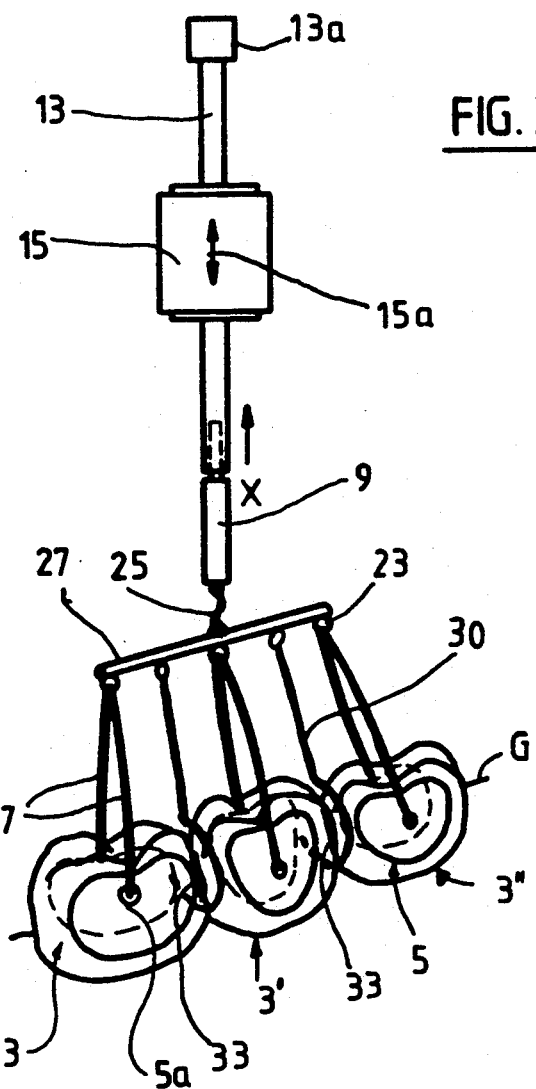
FIG. 3 is a perspective view of a third implement wherein the first unit comprises three pairs of jaws and two hooks, and the second unit includes a weighbeam pivotably mounting the hooks and the arms of the jaws.

The second unit of the implement 1 further comprises an elongated rod-like handle or handgrip member 9 one end of which carries the annular member 17 and the other end of which has an externally threaded stub 11 receivable in a tapped bore of a force applying member 13 indicated in FIG. 1 by a phantom line. FIG. 3 shows that the force applying member 13 is an elongated rod-shaped guide for a weight or hammer 15 which is reciprocable by hand in directions indicated by arrow 15a in order to repeatedly strike an anvil 13a at that end of the member 13 which is remote from the annular member 17. This results in repeated application of a selected pulling force in the direction of arrow X whereby the crown 3 is loosened and is ultimately separated from the respective tooth portion.

The annular member or eyelet 17 acts not unlike a joint which establishes an articulate connection between the two units of the implement 1 and enables the handle 9 of the second unit to change its orientation for more convenient reciprocation of the hammer 15 toward and away from the anvil 13a. Since the pads 5a of the jaws 5 engage two spaced apart portions of the external surface 3b of the crown 3 at opposite sides of the crown, the improved implement 1 is much less likely to tilt the crown in the course of the extracting operation. This not only reduces the likelihood of deformation of the crown 3 during extraction but also reduces the likelihood of damage to the bonding material which is used to secure the crown 3 to the portion of the tooth next to the tooth T of FIG. 1. Still further, the absence of undesirable tilting or other undesirable change of orientation of the crown 3 during extraction ensures that the force which is to be applied in order to extract the crown need not be increased in the course of the actual extracting operation; this will be readily appreciated since the crown 3 need not be tilted and/or otherwise misoriented while the hammer 15 repeatedly strikes the anvil 13a of the force applying member 13. In addition, and since the jaws 5 do not and need not come in contact with the edge 3a of the crown 3 and/or with the gums adjacent the edge 3a, the improved implement 1 is highly unlikely to cause discomfort to the patient and/or infection or inflammation or bleeding or swelling of the gums as a result of extraction of the crown 3 from a wearer's mouth.

The annular member or eyelet 17 can be replaced with other suitable means for establishing an articulate connection between the handle 9 of the second unit and the arms 7 of the jaws 5. For example, the annular member 17 can be replaced with a piece of flexible wire, with a piece of cord or the like to thus establish a universal joint which enables the handle 9 and the force applying member 13 to change their inclination relative to the arms 7 in any desired direction for more convenient manipulation of the sleeve 21, fastener or fasteners 21a and hammer 15.

The surfaces 19 of the pads 5a of the jaws 5 can have a concave or slightly concave shape in order to more accurately conform to the shapes of adjacent portions of the external surface 3b of the crown 3. The surface 19 of one of the jaws 5 need not be an exact mirror image of the other surface 19; all that counts is to configurate and/or coat and/or dimension the surfaces 19 in such a way that they can reliably engage and grip the crown 3 in the course of the extracting operation. The entire pads 5a of the jaws 5 can be made of a material which can be brought into highly satisfactory frictional engagement with the external surface 3b of a crown. However, it is also possible to make the pads 5a of the jaws 5 from a material which can reliably engage the crown 3 solely as a result of appropriate treatment (coating and/or roughening and/or shaping) of the surfaces 19).

The fastener or fasteners 21a can be omitted if the internal surface of the sleeve 21 is coated with a friction generating material (e.g., rubber) which ensures that the sleeve 21 will remain in a selected position, i.e., at a selected distance from the annular member 17.

The sleeve 21 can be replaced with an internally threaded nut which is to be rotated in order to move axially of the externally threaded arms 7 to a selected position in which the pads 5a of the jaws 5 are maintained in reliable frictional engagement with the adjacent portions of the external surface 3b of a crown 3.

Figure 2:
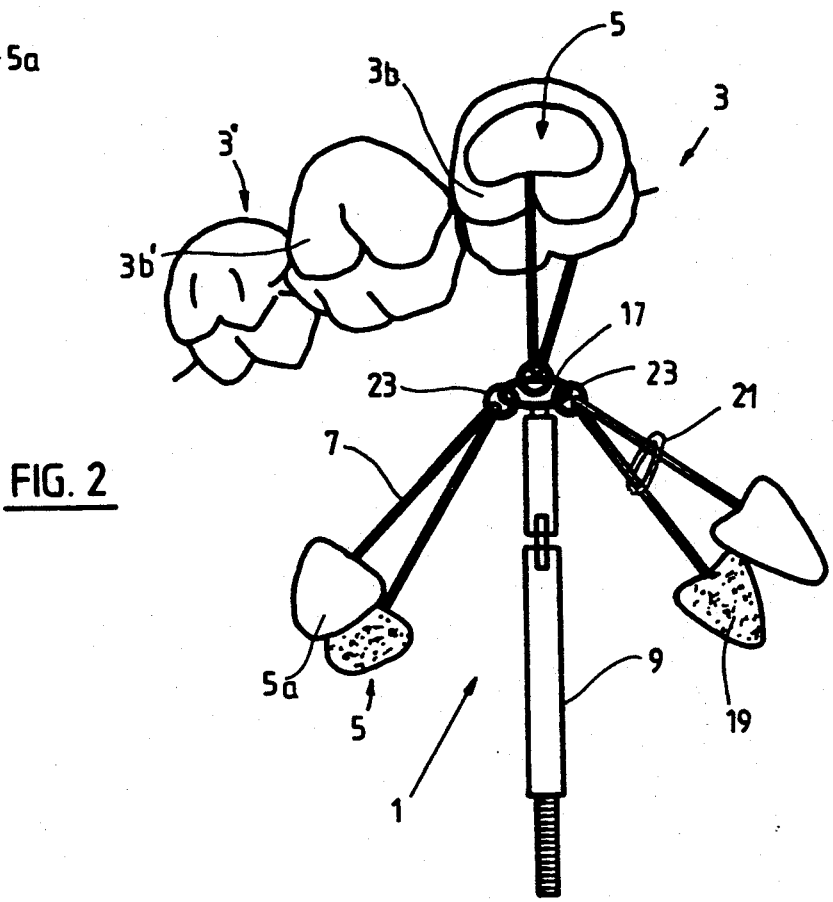
FIG. 2 is a perspective view of a second implement wherein the first unit comprises three pairs of jaws one of which is maintained in engagement with a crown.

The handle 9 of the second unit in the implement 1 of FIG. 2 carries an annular member or eyelet 17 for three discrete rings or eyelets 23. Each eyelet 23 receives the inner end portions of the arms 7 of a discrete pair of extracting elements or jaws 5. A sleeve 21 (only one shown) is provided for each pair of arms 7 to move the pads 5a of the respective jaws toward each other. The pads 5a of the median pair of jaws 5 which are shown in FIG. 3 are in frictional engagement with the external surface 3b of a crown 3. The dimensions and/or shapes of the pads 5a in each of the three pairs of jaws 5 are preferably different so that the dentist can select those pads which are best suited for satisfactory frictional engagement with the external surface 3b of a particular crown 3. A second pair of jaws 5 in the implement 1 of FIG. 2 can be used to engage the external surface 3b' of the crown 3' which is adjacent the crown 3, for example, when the crowns 3 and 3' are soldered or otherwise rigidly connected to each other to jointly form a bridge. The finish of the surfaces 19 on the pads 5a of one pair of jaws 5 of the three pairs which are shown in FIG. 2 can be different from pair to pair. This, too, contributes to versatility of the implement 1 which is shown in FIG. 2.

The annular member 17 and the three eyelets 23 together form what can be termed a universal joint which enables the handle 9 of the second unit of the implement 1 of FIG. 2 to change its orientation relative to one or more pairs of jaws 5 in engagement with one or more crowns in any desired direction. The construction of the force applying member 13 (not shown in FIG. 2) and of its anvil 13a and hammer 15 can be the same as shown in FIG. 3.

The implement of FIG. 3 differs from the implement 1 of FIG. 2 in that the second unit comprises a two-armed lever 27 which constitutes a weighbeam and is provided with rings or eyelets 23 for the arms 7 of the three pairs of jaws 5. In addition, the weighbeam 27 carries two hook-shaped extracting elements 30 (hereinafter called hooks) which alternate with the pairs of jaws 5 and can be used to engage the connectors 33 between pairs of neighboring crowns forming part of a bridge. The hooks 30 must be slipped under the connectors 33 and are thereupon pulled in a direction away from the gums G in order to detach the bridge from the corresponding teeth or portions of teeth in a patient's mouth.

A piece of flexible wire 25, an elastic band or a piece of cord is provided to connect the median portion of the weighbeam 27 to the handle 9.

FIG. 3 shows a bridge having three crowns 3, 3′, 3″ and two connectors 33 between such crowns. All of the extracting elements which are shown in FIG. 3 can be put to use simultaneously, i.e., each pair of jaws 5 can engage one of the three crowns and each of the two hooks 30 can engage one of the connectors 33. This ensures a highly satisfactory distribution of pulling forces and reduces the likelihood of misorientation of the bridge during extraction from a patient's mouth. Uniform distribution of pulling forces is also ensured by the rings or eyelets 23, weighbeam 27 and wire 25.

Each pair of jaws 5 and each of the two hooks 30 can be readily detached from the respective ring 23, i.e., the number of extracting elements of the first unit in the implement of FIG. 3 can be altered at will. If only the median pair of jaws 5 is retained, the implement 1 of FIG. 1 can be said to constitute a functional equivalent of the implement 1 which is shown in FIG. 1. The sleeves 21 were omitted in FIG. 3 for the sake of clarity.

Figure 4:
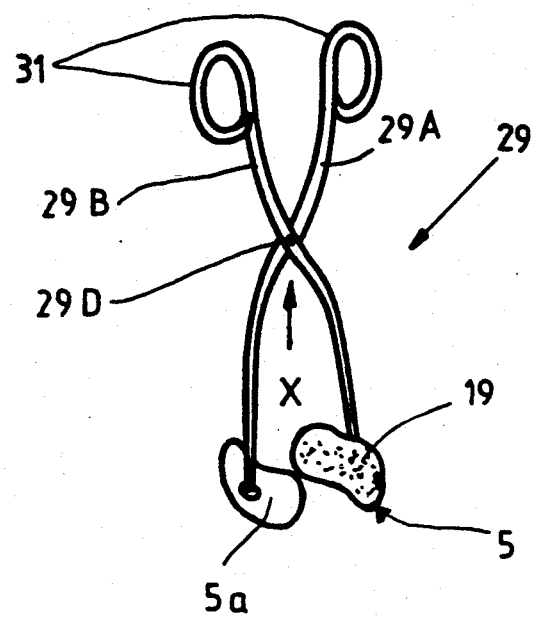
FIG. 4 is a perspective view of a fourth implement in the form of scissors with a single pair of jaws.

FIG. 4 shows an extracting implement 29 in the form of scissors 29. The two elongated halves 29A, 29B of the scissors 29 are pivotally connected to each other by a pin 29D, one end of each half carries a handle or handgrip portion 31, and the other end of each half carries a jaw 5, e.g., a jaw having a substantially kidney-shaped pad 5a. The user of the scissors 29 moves the pads 5a apart prior to engaging the surfaces 19 with adjacent portions of the external surface of a crown, and the handles 31 act not unlike the pulling force applying means 13 to extract a properly engaged crown from the mouth of a patient.

The lower portions of the halves 29A, 29B of the scissors 29 (as seen in FIG. 4) can be surrounded by a sleeve 21 or the like (not shown) in order to prevent any movement of the pads 5a away from each other in the course of the actual extracting operation, namely when the handles 31 are used to exert a pulling force in the direction of arrow X.

The sleeve 21 or sleeves 21 can be omitted, especially in an implement which employs a single pair of jaws 5, because the dentist can use two fingers of one hand to press the pads 5a against the external surface 3b of a crown 3 while the other hand operates the hammer 15 or exerts a pull upon the handles 31 in order to extract the crown.

The implement 29 of FIG. 4 can be used with particular advantage when a crown 3 is already loose, i.e., when it is not necessary to apply a pulsating force because the crown can be extracted by the simple expedient of exerting a single pull in the direction of arrow X. The implement of FIGS. 1, 2 or 3 can be used in the same way, i.e., it is not necessary to cause the hammer 15 to repeatedly strike the anvil 13a if the crown or bridge is loose so that it can be extracted with the exertion of a relatively small force.

Figure 5:
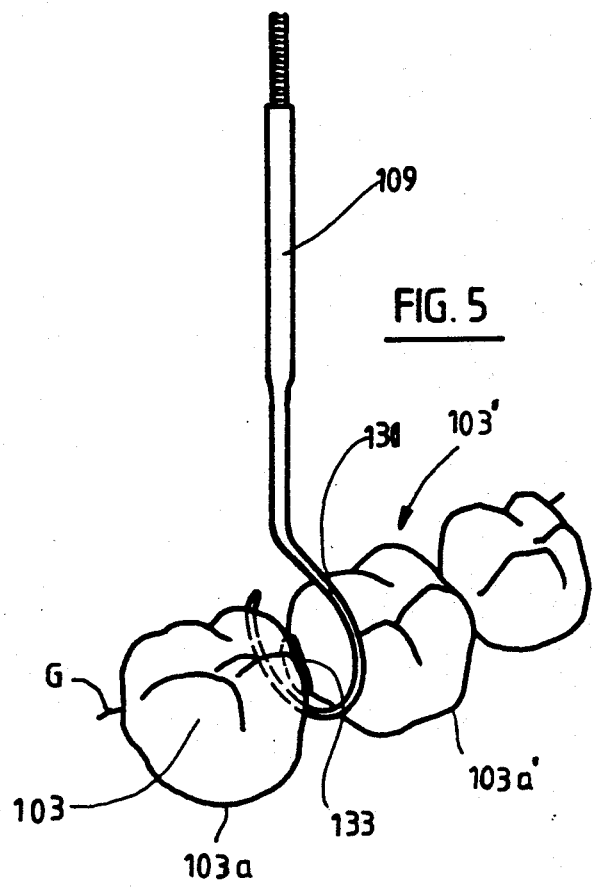
FIG. 5 is a perspective view of a portion of a further implement which is designed for extraction of bridges.

FIG. 5 shows as portion of a simple implement which can be used to loosen and extract a bridge composed of two crowns 103, 103′ and a connection or connector 133 between the crowns. The first unit of this implement comprises a single hook 130 of the type known as shepherd's crook which can be readily placed around the connector 133 without even touching the gums G and without coming close to the edges 103a, 103a′ of the crowns, and the handle 109 of the second unit is thereupon caused to exert a pull (e.g., by being connected to the force applying member 13 of FIG. 3) so that the bridge becomes separated from the corresponding teeth or fragments of teeth, and more particularly from the preparation which is used to bond the internal surfaces of the crowns 103, 103′ to the respective teeth.

The tip of the hook 130 is preferably rounded to further reduce the likelihood of injury to the gums G when the hook is caused to engage the connector 133. As a rule, the connector 130 is spaced apart from the edges 103, 103′ and from the gums G.

Figure 7:
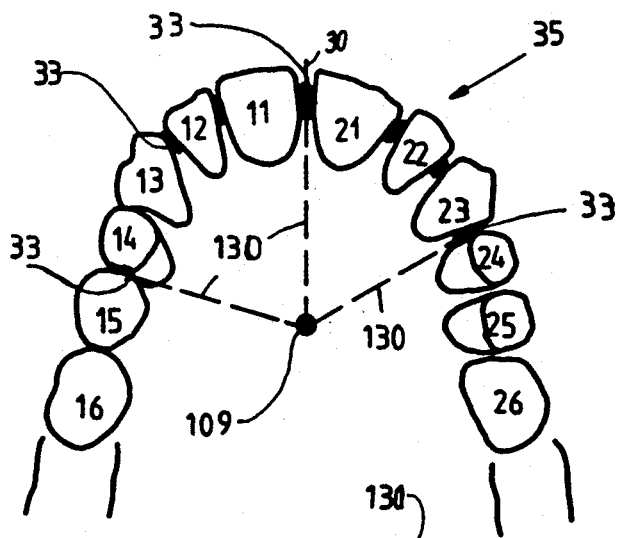
FIG. 7 is a plan view of a bridge which is composed of a substantial number of interconnected crowns and can be extracted with an implement of the type shown in FIG. 6.
Figure 6:
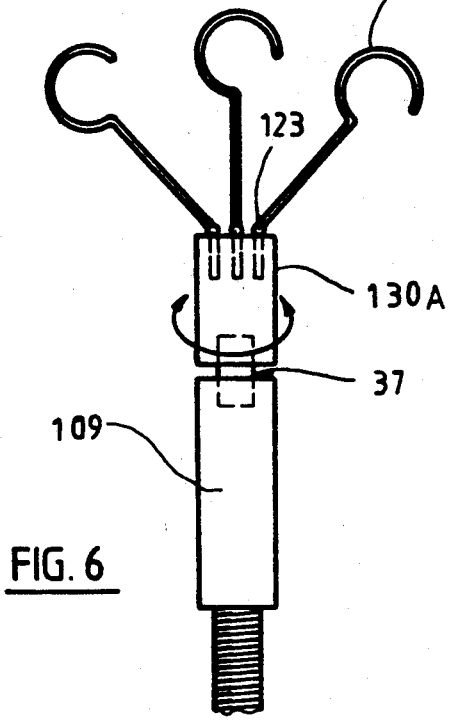
FIG. 6 is a fragmentary elevational view of a further implement which is also designed for extraction of bridges and wherein the first unit comprises three discrete hook-shaped extracting implements.

FIG. 6 shows a modified implement for removal of larger bridges, e.g., of a bridge 35 of the type shown in FIG. 7.

The first unit of the implement of FIG. 6 has three discrete extracting elements in the form of hooks 130 which are preferably articulately connected to the handle 109 of the second unit. For example, the connection between a holder 130A for the hooks 130 and the handle 109 can comprise a universal joint or any other suitable joint 37 (e.g., a piece of wire or cord or elastic band), and each hook 130 can be articulately connected to the holder 130A, e.g., by a ring or eyelet 123. This renders it possible to select the angular positions of the shanks of the hooks 130 practically at will and to thus ensure proper engagement between such hooks on the one hand and selected connectors 33 of the bridge 35 on the other hand.

The positions of the hooks 130 of FIG. 6 during engagement with three connectors 33 of the bridge 35 of FIG. 7 are indicated by broken lines. The crowns of the bridge 35 are numbered 11 to 16 and 21 to 26; the left-hand hook 130 engages a connector 33 between the teeth 14 and 15; the median hook 130 engages a connector 33 between crowns 11 and 21; and the right-hand hook 130 engages a connector 33 between the crowns 23 and 24. The number of hooks 130 can be reduced to two or one or increased to four or more, depending on the nature of the bridge which is to be extracted.

As already described with reference to FIG. 3, the first unit of the improved implement can include one or more hooks and one or more pairs of jaws; such implement can be used in lieu of the implement of FIG. 6 to even more reliably engage the bridge 35 at as many as eight different space-apart locations and to even further reduce the likelihood of tilting of the crowns 11 to 16 and 21 to 26 during extraction of the bridge 35.

A hook 30 or 130 can be replaced with an elongated flexible extracting element 215 of the type shown in FIGS. 8 to 10. This extracting element is a piece of wire 214 (preferably consisting of numerous metallic filaments, particularly steel filaments) with two ends which are provided with enlarged heads 217. The second unit of the implement of FIGS. 8 to 10 comprises a substantially flat rectangular or square housing or casing 209 having two lateral sockets each of which includes an elongated hole or bore 211, an elongated open slot 213 which extends from the respective hole 211 to the external surface of the housing 209, and an enlarged portion 219 for a head 217 of the flexible extracting element 215. The holes 211 are preferably parallel or nearly parallel to each other, and their diameters D are slightly larger than the diameter d of the wire 214 of the flexible element 215 but at least slightly smaller than the diameters of the enlarged portions 219.

The enlarged portions or heads 217 can be obtained by soldering, welding, press fitting or otherwise securing suitable sleeves or caps to the ends of the flexible element 215. The diameters of the heads 217 are selected in such a way that they fit snugly into the respective enlarged portions 219 while the adjacent portions or extremities 218 of the flexible element 215 are received in the holes 211 of the respective sockets. The width of the narrowest portions of the slots 213 (at the respective holes 211) can at least match the diameter d of the wire 214 of the flexible element 215 so that the extremities 218 of this element can be readily inserted into and withdrawn from the sockets in directions from the left and from the right, as seen in FIG. 8.

One of the heads 217 can be more or less permanently anchored in the housing 209. This can be seen in the right-hand portion of FIG. 8 where the enlarged portion 219 is tapped, as at 221, to accept the shank of a threaded fastener 223 serving to preferably releasably capture or confine the right-hand head 217 in the enlarged portion 219 of the respective socket. In addition to or in lieu of the fastener 223, the means for confining one of the heads 217 or both heads 217 in the enlarged portions 219 of the respective sockets can comprise a cover, closure or lid 224 (indicated in FIG. 8 by broken lines) pivotable to and from an operative position in which it overlies the adjacent ends of the sockets. It is also possible to employ a cover 224 having two arms one of which can be pivoted to and from a position of overlap with the right-hand head 217 and the other of which can be pivoted to and from a position of overlap with the left-hand head 217. The cover 224 can be provided with an opening or with two openings, each in register with one of the holes 211.

The housing 209 is provided with a recess 225 which is located between the sockets (and more specifically between the holes 211 in the housing), with a through hole or opening 229 adjacent the enlarged portions 219 of the sockets, and/or with yoke 233. The purpose of the recess 225 and/or hole 229 and/or yoke 233 is to permit engagement with a customary dentist's tool 235 (e.g., a hook at one end of a handle) or another dentist's tool 237, namely a stepped tool with a pallet at one end. Such tool or tools are used to exert upon the housing 209 a pull in a downward direction, as viewed in FIGS. 8 to 10. The recess 225 is preferably bounded in part by an inclined bottom surface 227, and the opening 229 can be bounded in part by an inclined bottom surface 231.

The operation of the implement of FIGS. 8 to 10 is as follows:

The fastener 223 is applied to secure the right-hand head 217 of FIG. 8 in the enlarged portion 219 of the respective socket. The left-hand head 217 is not confined in the housing 209 and can be caused to pass between the gums G and the connector 133 of the bridge including the crowns 103, 103' of FIG. 5 (or between the gums and any of the connectors 33 in the bridge 35 of FIG. 7). The flexible element 215 is then looped, and its exposed extremity 218 is introduced into the still unoccupied hole 211 so that the head 217 enters the enlarged portion 219 of the left-hand socket in the housing 209 of FIG. 8.

The surface bounding the recess 225, the surface bounding the opening 229 and/or the yoke 233 is then engaged by a tool 235 and/or 237 to exert a pull in the direction of arrow X and to thus exert a pull upon the connector 33 which is engaged by the bight of the looped flexible element 215 while the two heads 217 of the element 215 are securely anchored in the enlarged portions 219 of the respective sockets. If the dentist realizes that the engagement of the housing 209 by a tool 235 or 237 at the recess 225 is not very convenient or not the most satisfactory way of exerting a pull upon the looped flexible element 215, the dentist causes the tool to engage the surface bounding the opening 229 or to engage the yoke 233. Thus, the dentist has the option of selecting the application of a pulling force in a manner which is most convenient to the dentist and which ensures most convenient and painless extraction of a bridge.

The extremities 218 of the flexible element 215 can be dimensioned in such a way that they must be forced from the respective slots 213 into the adjacent holes 211. This greatly reduces the likelihood of accidental removal of such extremities from the respective sockets prior to tightening of the flexible element 215, i.e., prior to start of the actual extracting operation.

Two or more implements of the type shown in FIGS. 8 to 10 can be used simultaneously, e.g., in lieu of the hooks 130 which are shown in FIG. 6, to reduce the likelihood of tilting of crowns during extraction of a bridge having two or more connectors 33. If two or more implements of the type shown in FIGS. 8 to 10 are used, the dentist will preferably repeatedly switch from pulling with one of the looped flexible elements 215 to pulling with another flexible element 215 and so forth in order to reduce the likelihood of a change of orientation of the bridge in the course of an extracting operation.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. An implement for extracting dental prostheses of the type affixed to at least one tooth and having at least one portion spaced apart from the gums of the wearer, comprising a first unit including two extracting elements engageable with the at least one portion of the prosthesis to be extracted, each of said extracting elements including a jaw and each of said jaws having an elongated arm; and a second unit including means for applying to said extracting elements a force in a direction away from the gums of the wearer to thereby separate the prosthesis from the at least one tooth, said force applying means including means for moving said jaws between first positions in which said jaws provide room for the at least one portion of a prosthesis therebetween and second positions in which the jaws clamp the at least one portion of the prosthesis between them, said moving means comprising a sleeve which surrounds and is slidable along said arms.

2. The implement of claim 1, wherein said jaws include elastic prosthesis-engaging portions.

3. The implement of claim 1, wherein said jaws have roughened prosthesis-engaging surfaces.

4. The implement of claim 3, wherein said surfaces are connected with fragments of diamonds.

5. An implement for extracting dental prostheses of the type affixed to at least one tooth and having at least one portion spaced apart from the gums of the wearer, comprising a first unit including at least one extracting element engageable with the at least one portion of the prosthesis to be extracted, said at least one extracting element including an elongated flexible element having a first end and a second end; and a second unit including means for applying to said at least one extracting element a force in a direction away from the gums of the wearer to thereby separate the prosthesis from the at least one tooth, said force applying means comprising a housing having means for anchoring said ends therein subsequent to looping of said flexible element around the at least one portion of the prosthesis to be extracted.

6. The implement of claim 5, wherein said ends include heads and said anchoring means includes two spaced apart sockets provided in said housing, one for each of said ends and each having an enlarged portion for the respective head.

7. The implement of claim 6, wherein said anchoring means further comprises means for releasably confining at least one of said heads in the enlarged portion of the respective socket.

8. The implement of claim 7, wherein said confining means comprises a threaded member mating with said housing.

9. The implement of claim 7, wherein said confining means comprises a closure which overlies the enlarged portion of at least one of said sockets.

10. The implement of claim 6, wherein said flexible element has a first diameter and each of said sockets includes a hole having a second diameter slightly greater than said first diameter.

11. The implement of claim 10, wherein at least one of said heads has a diameter greater than said second diameter.

12. The implement of claim 5, wherein said second unit further comprises means for pulling said housing and said housing includes at least one portion which is engageable by said pulling means.

13. The implement of claim 12, wherein said at least one portion of said housing includes a recess.

14. The implement of claim 12, wherein said at least one portion of said housing includes a hole.

15. The implement of claim 12, wherein said at least one portion of said housing includes a yoke.

16. An implement for extracting dental prostheses of the type affixed to at least one tooth and having at least one portion spaced apart from the gums of the wearer, comprising a first unit including two extracting elements engageable with the at least one portion of the prosthesis to be extracted, each of said extracting elements including a jaw and each of said jaws having an elongated arm; and a second unit including means for applying to said extracting elements a force in a direction away from the gums of the wearer to thereby separate the prosthesis from the at least one tooth, said force applying means including means for moving said jaws between first positions in which said jaws provide room for the at least one portion of a prosthesis therebetween and second positions in which the jaws clamp the at least one portion of the prosthesis between them, said moving means including an internally threaded nut surrounding said arms.

17. An implement for extracting dental prostheses of the type affixed to at least one tooth and having at least one portion spaced apart from the gums of the wearer, comprising a first unit including a plurality of extracting elements engageable with the at least one portion of the prosthesis to be extracted; and a second unit including means for applying to said extracting elements a force in a direction away from the gums of the wearer to thereby separate the prosthesis from the at least one tooth, said force applying means comprising means for movably coupling said extracting elements to each other and said coupling means comprising at least one annular member.

18. The implement of claim 17, wherein said second unit includes shears having two elongated halves each having a handle at one end and carrying one of said jaws at the other end, and means for pivotally connecting said halves to each other intermediate said ends thereof.

19. An implement for extracting dental prostheses of the type affixed to at least one tooth and having at least one portion spaced apart from the gums of the wearer, comprising a first unit including a plurality of extracting elements engageable with the at least one portion of the prosthesis to be extracted; and a second unit including means for applying to said extracting elements a force in a direction away from the gums of the wearer to thereby separate the prosthesis from the at least one tooth, said force applying means comprising means for movably coupling said extracting elements to each other and said coupling means comprising at least one weighbeam.

* * * * *